United States Patent [19]
Westerman

[11] Patent Number: 4,642,053
[45] Date of Patent: Feb. 10, 1987

[54] PILLAR CUSP

[76] Inventor: Robert D. Westerman, 7 Oak Alley, Baton Rouge, La. 70806

[21] Appl. No.: 723,737

[22] Filed: Apr. 16, 1985

Related U.S. Application Data

[63] Continuation of Ser. No. 524,578, Aug. 19, 1983, abandoned.

[51] Int. Cl.⁴ .............................................. A61C 5/04
[52] U.S. Cl. ................................................... 433/225
[58] Field of Search .............. 433/225, 174, 176, 220, 433/221

[56] References Cited

U.S. PATENT DOCUMENTS

| 400,921 | 4/1889 | Land | 433/225 |
| 3,082,525 | 3/1963 | Christensen | 433/174 |
| 3,728,794 | 4/1973 | Edelman | 433/225 |
| 3,837,080 | 9/1974 | Pasqualin | 433/176 |
| 4,016,651 | 4/1977 | Kawahara et al. | 433/174 |
| 4,219,620 | 8/1980 | Carse | 433/225 |
| 4,331,423 | 5/1982 | Yanney, Jr. | 433/225 |

Primary Examiner—John J. Wilson
Attorney, Agent, or Firm—Blakely, Sokoloff, Taylor & Zafman

[57] ABSTRACT

A method and apparatus is disclosed for use by dental practitioners to enable the restoration of decayed or damaged teeth. The method comprises preparing the tooth for installation of the disclosed apparatus, which will be referred to herein as a pillar cusp, by removing decay, old restorations and damaged tooth structure, and then preparing a horizontally disposed, flat circular area or niche on the dentin for each cusp to be restored. The flat circular area should be approximately centered on an axis located through that of the removed cusp. A vertically disposed channel is then drilled at the center of the niche and a self-threading dental anchoring device or screw is inserted into the channel. The pillar cusp, which, in effect, is an artificial or man-made dentin, is then threaded onto the screw. After any necessary adjustments have been made to properly seat the pillar cusp, impressions are taken and the crown or onlay used to complete the restoration is then secured to the pillar cusp or pillar cusps, if more than one cusp has been restored. The pillar cusp itself comprises a metallic, frustum shaped device, threaded through its longitudinal axis for threading onto the above-mentioned dental anchor such that its base lies flush on the circular, flattened area of the dentin.

10 Claims, 4 Drawing Figures

PILLAR CUSP

This is a continuation of application Ser. No. 524,578 filed Aug. 19, 1983 now abandoned.

BACKGROUND OF THE INVENTION

The present invention relates to a method and apparatus for the restoration of a tooth with a fractured cusp or a tooth that has been previously restored on several surfaces.

In such situations, the tooth is usually weakened and in need of crown restoration because, after the tooth has been excavated by the removal of old restoration material and/or decayed or defective tooth structure, there is often insufficient structure left to allow the utilization of a conventional cast crown. To address this problem, modern dental practice generally utilizes one of three techniques for restoring a tooth which is in a weakened condition as described above. These three techniques are known as:

(a) cast crown with parallel iridio-platinum or cast pin retention utilizing cemented pins;

(b) combination of a pin-retaining device, which may be a cemented, friction lock or self-threading pin, and amalgam buildup restoration;

(c) pin-retained foundation of amalgam or composite resin covered with a cast crown.

Each of these techniques has its disadvantages, which disadvantages do not exist with the method and apparatus taught herein. In particular, with respect to technique (a), cemented pins are substantially less retentive than self-threading pins or friction lock pins. This technique requires much impression-taking and model-construction utilizing the pins. Further problems include seating the crown accurately, drying and varnishing the pin holes in the dentin for the pins, and cementing the crown to the pins.

With respect to method (b), there are two main disadvantages namely, (i) the difficulty of rebuilding the tooth into proper occlusion, while retaining good natural contacts and contours; and (ii) the inherent weakness of amalgam to survive for long periods of time in the mouth. It is believed that the compressive strength of this type of restoration is not increased by the placement of pins. Additionally, the pins used for this technique decrease the transverse and tensile strength of amalgam. This technique also requires the placement of multiple pins. It is known that when more than one pin is placed in a tooth, the potential for dental crazing, damage, fracture, pulp devitalization and tooth loss increases substantially.

The main disadvantage of technique (c) is the hydrophilic property of all commercially available composite resins which which results in the resin material absorbing water and oral fluids. Any space between the restored tooth and the composite resin becomes filled with fluid when contacted by water or saliva. Once wet, it is difficult, if not impossible, to dry the composite resin in the space before cementation. The moisture causes the cement to be leached out and leaves it chalky and permeable. Hydrophobic fluorindated composites have been developed, but are not presently commercially available.

The present invention avoids most, if not all of the disadvantages of the prior art techniques and, as will be discussed below, has many advantages over the prior art techniques.

Prior art references of interest are as follows: U.S. Pat. Nos. 400,921, 1,018,803, 3,675,328, 3,728,794, 3,831,281, 4,202,101, 4,259,076 and 4,331,423 each of which teaches pin or screw anchoring devices used for dental restorations.

SUMMARY OF THE INVENTION

A method and apparatus is disclosed for use by dental practitioners to enable the restoration of decayed or damaged teeth. The method comprises preparing the tooth for installation of the disclosed apparatus, which will be referred to herein as a pillar cusp, by removing decay, old restorations and damaged tooth structure, and then preparing a horizontally disposed, flat circular area or niche on the dentin for each cusp to be restored. The flat circular area should be approximately centered on an axis located through that of the removed cusp. A vertically disposed channel is then drilled at the center of the niche and a self-threading dental anchoring device or screw is inserted into the channel. The pillar cusp, which, in effect, is an artificial or man-made dentin, is then threaded onto the screw. After any necessary adjustments have been made to properly seat the pillar cusp, impressions are taken and the crown or onlay used to complete the restoration is then secured to the pillar cusp or pillar cusps, if more than one cusp has been restored. The pillar cusp itself comprises a metallic, frustum shaped device, threaded through its longitudinal axis for threading onto the above-mentioned dental anchor such that its base lies flush on the circular, flattened area of the dentin.

DETAILED DESCRIPTION OF THE INVENTION

Figure 1:
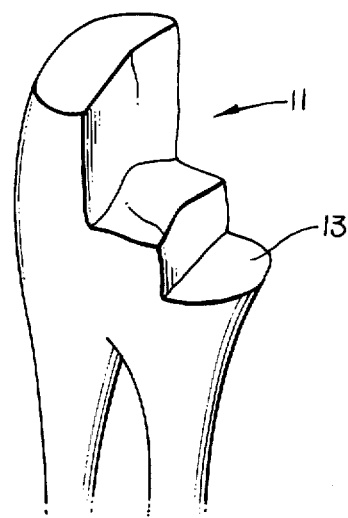
FIG. 1 is a perspective view of a tooth which has been excavated.

With reference to the drawings, FIG. 1 shows a tooth 11, wherein old restorations, decay and defective tooth structure have been removed by well known prior art techniques. The tooth represented in the Figures is shown as described with respect to the removal and restoration of a single cusp. However, it is to be understood that the description set forth herein has equal application with respect to the restoration of two, three or four cusps of a particular tooth. In the area of the missing cusp, a horizontally disposed, flat and generally circular area or niche 13 is formed in the dentin to accommodate the base of the pillar cusp as described hereinbelow. The size of the niche 13 should be approximately 2.0 mm in diameter for small bicuspids and approximately 2.5 mm for large bicuspids and molars.

At the center of the niche 13, an approximately 2.5 mm deep channel 15 for inserting a dental anchoring pin 19 is drilled perpendicular to and centered on the niche. A reference which contains diagrams showing proper pin location may be found in Courtade and Timmermans, "Pins in Restorative Denistry," published in 1971 by the C.B Bosby Company. After the channel has been drilled, cavity varnish should be placed in the channel to prevent micro-leakage. At this point, the pin 19 may be installed. The pin 19 should be inserted into the full 2.5 mm depth of channel and should extend between approximately 1.2 mm and 2.5 mm from the surface of niche 13, such that it extends at least one-half the height (as set forth hereinbelow) of the pillar cusp 21 to be installed thereon.

A pin which is known to work properly in conjunction with the disclosed pillar cusp is described in U.S. Pat. No. 4,202,101 issued to Weissman, which is sold as the Whaledent Link Series L541 Regular. Additionally, the Whaledent Regular 2-in-1 self-threading and self-shearing pin has been successfully used. Neither of these pins are crimped on the exposed end (after installation) as are regular TMS pins, which are so crimped for ease of installation with a wrench or chuck of an auto clutch handpiece. If the pin is so crimped, the pillar cusp cannot be threaded onto the pin without first cutting off the crimped end, which may dislodge the pin from its channel in the dentin or weaken its retention. For this reason, the self-shearing pins described above are recommended.

Once the pin 19 has been installed, the disclosed pillar cusp 21 may be trial placed on the pin. When the pillar cusp is properly placed, it will screw down on the pin such that its base 23 lies flush on the exposed dentin of niche 13, thereby securing the pin and bracing the pillar cusp on the dentin.

In view of the relatively small size of the pillar cusp, the pillar cusp should be held by a chuck before placement on the pin. In this connection, any commercially available chuck may be used to hold the pillar cusp so that it can be placed on the pin and screwed into position. If the pillar cusp 21 seats properly on the dentin of niche 13, if alteration or reduction of the pillar cusp is needed, it should be cemented to seal the area between the exposed dentin and the base of the pillar cusp after it has been placed on the pin and tooth. The cement is not necessary, however, if the pillar cusp is the proper size and requires no alteration or reduction. That is, if it is necessary to alter the size of the pillar cusp, the rotary action of a dental bur can unscrew the pillar cusp from the pin at a very high rate of speed. It is preferable that the cement set within a few seconds so that the pillar cusp may be altered or reshaped, if necessary, with a high speed hand piece without the pillar cusp screwing back off the pin. In this connection, cyanoacrylate cement has been found to perform satisfactorily. It is to be noted that the threads of the pillar cusp and pin are not cemented.

If the pillar cusp 21 does not seal properly, it should be removed by threaded disengagement from the pin 19. Once the obstruction has been removed and/or the niche 13 widened to accommodate the pillar cusp, the pillar cusp may be reinstalled on the pin.

After the pillar cusp has been properly seated and, if necessary, cemented, and altered, the dental restoration, that is installation of a crown or onlay, may be completed utilizing the dental practitioner's preferred technique and materials.

The pillar cusp 21 itself, is fabricated utilizing materials frequently employed in the dental art such as precious metal or alloy of gold, silver or platinum, or a non-precious metal or alloy of stainless steel, chromium-nickel or cobalt-chromium, titanium and the like. The pillar cusp 21 is a frustum, preferably conical, with a bore 25 through its longitudinal axis. The bore need not extend the length of the pillar cusp. Of course, if the bore does not extend the length of the pillar cusp, the open end of the bore should be at the base of the pillar cusp. The bore 25 should be threaded at least to the depth of the pin 19 extending from the dentin.

Figure 4:
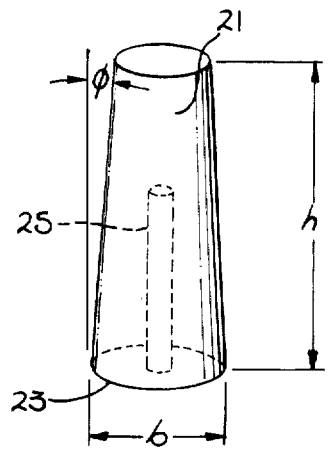
FIG. 4 is an enlarged perspective view of the pillar cusp of the subject invention.
Figure 2:
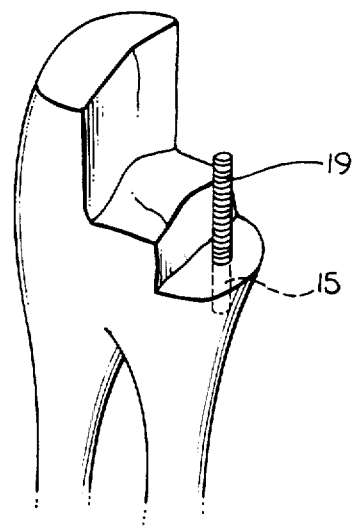
FIG. 2 is a perspective view of an excavated tooth which has a pin inserted into its dentin, the pin positioned to accept the pillar cusp of the subject invention.
Figure 3:
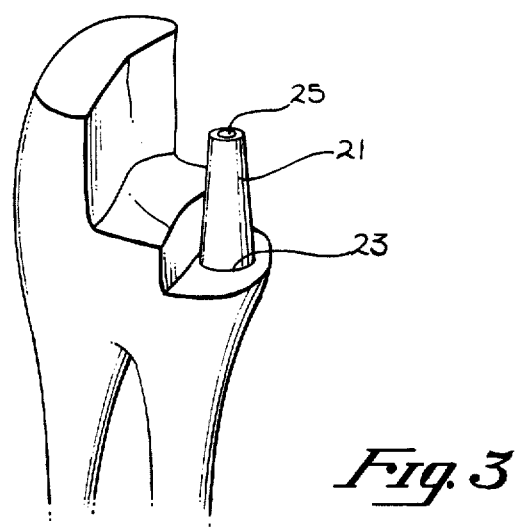
FIG. 3 is a perspective view of the pillar cusp of the subject invention shown mounted on a tooth to be restored.

The dimensions of the pillar cusp depend on the intended use. With reference to FIG. 4, the diameter b of the pillar cusp will vary between approximately 1.9 mm (0.075") and 2.5 mm (0.098") and the height h of the pillar cusp will vary between approximately 2.5 mm (0.098") and 5 mm (0.1968"). Generally, the shorter the pillar cusp, the greater the degree of side taper $\phi$, up to a maximum of approximately 4°, and the longer the pillar cusp, the smaller the degree of side taper, down to a minimum of approximately 3°. Dimensions which have been found to provide satisfactory results for particular applications are shown in TABLE I:

TABLE 1

| BASE DIAMETER | HEIGHT | SIDE TAPER | APPLICATION |
| --- | --- | --- | --- |
| .075" (1.9 mm) | .140 (3.55 mm) | 3° | Small bicuspids |
| .085" (2.15 mm) | .160 (4.0 mm) | 3¼° | Bicuspids |
| .092" (2.33 mm) | .160 (4.0 mm) | 3° | Large Bicuspids and small molars |
| .092" (2.33 mm) | .125 (3.2 mm) | 3° | Molars |

Of course, these dimensions may be altered by the dental practitioner to suit a particular application.

Pillar cusps of the proper dimensions, taper and thread can be fabricated by a machinist using #309 stainless steel and a Whaledent tap, Catalog #S-17E.

Thus, a novel pillar cusp and method for installing the pillar cusp have been disclosed. It should be understood that particular preferred materials and dimensions have been disclosed herein for purpose of illustration and are not to be construed as limiting the scope of the invention as defined in the claims set forth below.

I claim:

1. An apparatus for use in connection with tooth restoration, specifically the restoration of one or more cusps of a tooth, comprising a frustum with a bore through its base, said bore being at least partially threaded, the threaded portion thereof beginning at said base of said frustrum, and a dental anchoring pin, one end of which is for inserting in a channel drilled into the dentin portion of said tooth being restored, the other end of said pin threadedly engaging the threaded portion of said bore, wherein the diameter of said base of said frustum ranges between approximately 1.9 mm and 2.5 mm, the height of said frustum ranges between approximately 2.5 mm and 5.0 mm, and the angle of the side taper of said frustum ranges between approximately 3° and 4°.

2. The apparatus defined by claim 1 wherein said frustrum is conical.

3. The apparatus defined by claim 1 wherein said bore coincides with the longitudinal axis of said frustum, extending at least partially therethrough.

4. The apparatus defined by claim 1 where the diameter of said base is approximately 1.9 mm, the height of said frustum is approximately 3.55 mm and the angle of the side taper of said frustum is approximately 3°.

5. The apparatus defined by claim 1 where the diameter of said base is approximately 2.15 mm, the height of said frustum is approximately 4.0 mm and the angle of the side taper of said frustum is approximately 3¼°.

6. The apparatus defined by claim 1 where the diameter of said base is approximately 2.33 mm, the height of said frustum is approximately 4.0 mm and the angle of the side taper of said frustum is approximately 3°.

7. The apparatus defined by claim 1 where the diameter of said base is approximately 2.33 mm, the height of said frustum is approximately 3.2 mm and the angle of the side taper of said frustum is approximately 3°.

8. The apparatus defined by claim 1 wherein said pin is a self-shearing pin.

9. A method for restoring one or more cusps of a decayed or otherwise damaged tooth comprising the steps of
  (a) removing the decayed or damaged tooth structure;
  (b) preparing a horizontally disposed, generally circular niche in a portion of the dentin of the tooth corresponding to the area of each missing cusp;
  (c) drilling a channel approximately centered on said niche and perpendicular thereto;
  (d) inserting a threaded dental anchoring device in said channel;
  (e) threading a conical frustum on said anchoring device such that the base of said frustum lies flush with the exposed dentin of said niche; and
  (f) installing an onlay or crown on said frustum.

10. The method defined by claim 9 further comprising the step of cementing the base of said frustum to the exposed dentin and altering the shape of said frustum prior to installing said onlay or crown.

* * * * *

UNITED STATES PATENT AND TRADEMARK OFFICE
CERTIFICATE OF CORRECTION

PATENT NO. : 4,642,053

DATED : 2/10/87

INVENTOR(S) : WESTERMAN

It is certified that error appears in the above-identified patent and that said Letters Patent is hereby corrected as shown below:

| COLUMN | LINE | DESCRIPTION |
|--------|------|-------------|
| 4 | 9 | delete "h" insert--$\underline{h}$-- |
| 4 | 7 | delete "b" insert--$\underline{b}$-- |

Signed and Sealed this

Fifth Day of July, 1988

Attest:

DONALD J. QUIGG

Attesting Officer      Commissioner of Patents and Trademarks